United States Patent [19]

Huston et al.

[11] Patent Number: 5,243,040
[45] Date of Patent: Sep. 7, 1993

[54] DNA ENCODING A PROTEIN WHICH ENABLES SELECTIVE REMOVAL OF IMMUNE COMPLEXES

[75] Inventors: James S. Huston, Chestnut Hill; Lynn Baird, Belmont; Charles Cohen; Hermann Oppermann, both of Medway, all of Mass.

[73] Assignee: Creative BioMolecules, Hopkinton, Mass.

[21] Appl. No.: 787,669

[22] Filed: Nov. 4, 1991

Related U.S. Application Data

[60] Division of Ser. No. 601,029, Oct. 23, 1990, Pat. No. 5,084,398, which is a continuation of Ser. No. 123,224, Nov. 20, 1987, abandoned.

[51] Int. Cl.$^5$ .................... C12N 15/31; A61K 37/00; A61K 37/02
[52] U.S. Cl. ................... 536/23.4; 530/387.1; 530/387.9; 530/391.1; 530/324; 436/535; 436/538; 424/858; 604/6; 435/7.1
[58] Field of Search ............ 536/27, 23.4, 387.1, 536/387.9, 391.1; 530/324, 387; 436/535, 538; 604/6; 435/7, 7.1; 424/85.8; 514/12

[56] References Cited

U.S. PATENT DOCUMENTS

| | | | |
|---|---|---|---|
| 4,614,513 | 9/1986 | Bensinger | 604/6 |
| 4,687,734 | 8/1987 | Chester | 435/7 |
| 5,084,398 | 1/1992 | Huston et al. | 530/324 |

FOREIGN PATENT DOCUMENTS

| | | |
|---|---|---|
| 0107509 | 3/1984 | European Pat. Off. . |
| 0200909 | 12/1986 | European Pat. Off. . |
| 0230869 | 8/1987 | European Pat. Off. . |
| 0284368 | 9/1988 | European Pat. Off. . |
| 8300297 | 2/1983 | World Int. Prop. O. . |
| 8300298 | 2/1983 | World Int. Prop. O. . |
| 8400773 | 3/1984 | World Int. Prop. O. . |
| 8400774 | 3/1984 | World Int. Prop. O. . |
| 8403103 | 8/1984 | World Int. Prop. O. . |
| 8705025 | 8/1987 | World Int. Prop. O. . |
| 8705631 | 9/1987 | World Int. Prop. O. . |

OTHER PUBLICATIONS

Uhlen et al., Gene 1983, 23:369-378.
Selective Affinity of Protein A Containing Staphylococci for Monomeric & Polymeric IgG, Maria-Ana Dobre et al., Journal of Immunological Methods, vol. 66, pp. 171-178, 1984.

*Primary Examiner*—Robert J. Hill, Jr.
*Assistant Examiner*—Shelly Guest Cermak
*Attorney, Agent, or Firm*—Testa, Hurwitz & Thibeault

[57] ABSTRACT

Disclosed is a method and a family of materials useful for removing immune complexes from blood preferentially to soluble antibodies. The material comprises analogs of proteins which bind to the Fc region of immunoglobulin. The analogs are produced by truncating or otherwise altering the amino acid sequence of the binding protein to reduce their affinity for Fc. An array of such analogs disposed about the surface of an insoluble matrix has the ability to form multiple points of attachment to the multiple Fc's in a complex so as to bind complex strongly, whereas only weak associations are developed between the Fc region of soluble IgG and individual analogs. The preferred analogs are truncated proteins homologous to a portion of the domains of Protein A or Protein G which bind with Fc. Complex may be removed from whole blood or serum using the material and conventional plasmapheresis techniques.

3 Claims, 3 Drawing Sheets

```
START          10          20          30
ATGGCTGACAACAAATTCAACAAGGAACAGCAGAAC
MetAlaAspAsnLysPheAsnLysGluGlnGlnAsn
 M   A  D  N  K  F* N* K  E  Q* Q  N 40          50          60
GCGTTCTACGAGATCTTGCACCTGCCGAACCTGAAC
AlaPheTyrGluIleLeuHisLeuProAsnLeuAsn
 A   F* Y  E  I  L* H* L  P  N  L  N 70          80          90         100
GAAGAGCAGCGTAACGGCTTCATCCAAAGCTTGAAA
GluGluGlnArgAsnGlyPheIleGlnSerLeuLys
 E   E  Q  R  N  G  F* I* Q  S  L* K 110         120         130          I
CACGACCCGTCTCAGAGCGCTAACCTGCTGGCAGAG
AspAspProSerGlnSerAlaAsnLeuLeuAlaGlu
 D   D  P  S  Q  S  A  N  L  L  A  E 40         150         160         170
GCCAAGAAACTGAACGACGCTCAGGCGCCGAAG
AlaLysLysLeuAsnAspAlaGlnAlaProLys
 A   K  K  L  N  D  A  Q  A  P  K
```

*FIG. 1A*

| | |
|---|---|
| FB-58 | ADNKFNKEQQNAFYEILHLPNLNEEQRNGFIQSLKDDPSQSANLLAEAKKLNDAQAPK |
| FB-TF | EQQNAFYEILHLPNLNEEQRNGFIQSLKDDPSQSANLLAEAKKLNDAQAPK |
| FB-36 | ADNKFNKEQQNAFYEILHLPNLNEEQRNGFIQSLKD |
| FB-29 | EQQNAFYEILHLPNLNEEQRNGFIQSLKD |
| FB-40 | EQQNAFYEILHLPNLNEEQRNGFIQSLKDDPSQSANLLAE |
| FB-47 | ADNKFNKEQQNAFYEILHLPNLNEEQRNGFIQSLKDDPSQSANLLAE |

*FIG. 1B*

```
         10          20         30          40
ATGCCGCCATGCGCAGCTGAACAGCAGAACGCGTTCTACGAGATCTTG
MetProProCysAlaAlaGluGlnGlnAsnAlaPheTyrGluIleLeu
 M  P  P  C  A  A  E  Q  Q  N  A  F  Y  E  I  L 50         60         70         80         90         100
CACCTGCCGAACCTGAACGAAGAGCAGCGTAACGGCTTCATCCAAAGCTTGAAAGACTAA
HisLeuProAsnLeuAsnGluGluGlnArgAsnGlyPheIleGlnSerLeuLysAsp*oc
 H  L  P  N  L  N  E  E  Q  R  N  G  F  I  Q  S  L  K  D
```

*FIG. 2*

DNA ENCODING A PROTEIN WHICH ENABLES SELECTIVE REMOVAL OF IMMUNE COMPLEXES

This is a divisional of copending application(s) Ser. No. 07/601,029 field on Oct. 23, 1990, now U.S. Pat. No. 5,084,398, which is file-wrapper continuation of U.S. Ser. No. 07/127,224 filed Nov. 20, 1989 now abandoned.

BACKGROUDN OF THE INVENTION

This invention relates to novel compositions of matter useful in the selective removal of immune complexes from serum. More specifically, this invention relates to an immunosorbent material comprising plural polypeptide domains designed to bind immune complex with greater affinity than free, circulating immunoglobulin.

Immune complexes have been implicated in the pathology of a number of human disease states. Indeed, the serum of many individuals with autoimmune disease, neoplastic disease, acquired immune deficiency syndrome, and some infectious diseases can be demonstrated to contain high levels of circulating immune complexes. Such complexes have been hypothesized to mediate a variety of immunologic effector functions. Removal of the complexes from circulating blood is expected to have therapeutic benefit.

U.S. Pat. No. 4,614,513 describes a method and apparatus for removing "immunoreactive substances" from blood comprising at least "components of Protein A". Protein A is a cell wall component of most strains of Staphylococcus aureus which has the capacity to bind specifically to the Fc region of a number of immunoglobulin species. The native protein is partially buried in the cell wall via its hydrophobic N-terminal segment which consists of about 150 amino acid residues. The remainder of the molecule consists of five highly homologous domains designated E, D, A, B, and C, which are consecutively arranged along the polypeptide chain, each having a molecular weight of approximately 7000 daltons. Each domain has the capacity to independently bind one Fc region of an immunoglobulin with apparently equal affinity. This binding interaction has an association or binding constant ($K_a$) of approximately $5 \times 10^7 M^{-1}$, which varies slightly with the pH of the buffer and with the species, class, and subclass of the immunoglobulin. However, Protein A is able to bind only two immunoglobulin molecules at one time, presumably due to steric constraints.

The binding of Protein A to the Fc region of an immunoglobulin has no significant effect on the affinity of the immunoglobulin for its antigen. Protein A from native and recombinant sources accordingly is useful as an immunosorbent for a variety of diagnostic and basic research applications. See European Patent No. 83306500.6 and International Patent Application Nos. PCT/SE/83/00297 and PCT/SE83/00298. These applications disclose "Protein A-like" molecules with substantially the same "Protein A-like binding" or increased "IgG-binding activity".

Unrecognized in the disclosure of U.S. Pat. No. 4,614,513 is the constraint on the method there disclosed that Protein A binds both free and complexed immunoglobulin. Thus, Protein A cannot be used practically as a therapeutic reagent to selectively remove immune complexes in the presence of uncomplexed, soluble immunoglobulin.

It is an object of this invention to provide a novel immunosorbent material which is useful, for example, in the selective removal of immune complexes from blood or serum. Another object is to provide a DNA sequence encoding this immunosorbent polypeptide, and to provide a method for the removal of immune complexes from serum in the presence of free, circulating immunoglobulins.

These and other objects and features of the invention will be apparent from the following description, drawing, and claims.

SUMMARY OF THE INVENTION

A strategy has now been devised which allows for the selective removal of immune complexes, i.e., aggregates of immunoglobulin molecules, from serum. In a preferred aspect, the strategy utilizes the natural ability of staphylol Protein A and its individual binding domains to bind to the Fc portion of an immunoglobulin without affecting the affinity of that immunoglobulin for its antigen. It also takes advantage of known recombinant DNA manipulative techniques to alter the structure of the native Protein A binding domain such that it has the capacity to bind to cross-linked, complexed, or aggregated immunoglobulins (complex) with greater affinity than it binds to free, soluble immunoglobulins (sol-Ab).

In accordance with the invention, it has been discovered that material comprising plural copies of an analog of a binding domain of Protein A having reduced affinity for sol-Ab relative to Protein A, i.e., havin $K_a$'s less than $10^7 M^{-1}$ and preferably less than $10^5 M^{-1}$, demonstrate a selective preference for immune complexes. The material is characterized by multiple interactions between plural binding domains and plural Fc's on different immunoglobulins within the immune complex. Multiple points of attachment to an immune complex form when a single molecule contains plural copies of a binding domain spaced sufficiently apart, i.e., at least about 52 angstroms, so that multiple point binding is permitted. Alternatively, monomeric binding sites are immobilized on a solid support at a threshold concentration such that binding sites are spaced apart on the surface of the matrix permitting multiple point attachment with complex. The $K_a$ characteristic of the binding between a single binding domain and a single Fc is quite low, but the presence of multiple interactions characteristic of the material of the invention results in a molecular association having significant stability, with an effective binding constant approaching the product of the individual constants of the individual binding domains.

Support for the hypothesis on which the invention is based can be found in the literature. For example, J. J. Langone and others (Langone, Adv. Immunol., 32:157-252, 1982 and Dobre et al. J. Immunol. Meth., 66:171-178, 1984) have demonstrated that soluble IgG from species which bind weakly to Protein A (e.g. mouse and goat), interact with higher affinity when the immunoglobulins are aggregated to form complex. Similarly, it is known that the first component of the complement cascade, Clq, has a low affinity for the Fc portion of IgG, and that it is not bound significantly to soluble IgG molecules. Because Clq molecules are composed of six binding sites, all having identical specificity for Fc, it is thought that the binding of a single Clq and three or more Fc's (associated in an immune complex) is responsible for the formation of an extremely stable structure (Hughes-Jones, Immunol., 32:191-198, 1977; Hughes-Jones and Gardner, Mol. Immunol., 16:697-701, 1979).

Multiple, reduced-binding analogs may be covalently attached to a support matrix at a density which is more conducive to binding complex than it is to binding sol-Ab. This attachment can be done using an appropriate amino acid capable of reacting with a heterobifunctional cross-linker covalently attached to the matrix, which itself has no immunoglobulin-binding capabilities.

In accordance with the invention, complexed immunoglobulins can be selectively removed from plasma in the presence of uncomplexed immunoglobulin by separating the blood into its plasma and cellular components, exposing the plasma to the immunosorbent material, and recombining the treated plasma with the cellular component.

These and other features of the invention will be apparent from the following description, figures, and claims.

BRIEF DESCRIPTION OF THE DRAWING

FIG. 1A shows a DNA sequence and the amino acid sequence (in both single letter and three letter code) of the FB binding domain of native Protein A. Underlined residues indicate the alpha helical regions; starred residues identify those which come closest to residues in the Fc region of human IgG during binding;

FIG. 1B discloses the amino acid sequences (in single letter code) of native $FB_{58}$) and FB analogs of the invention having reduced binding affinities for soluble IgG, including truncated analogs $FB_{TF}$, $FB_{36}$, $FB_{29}$, $FB_{40}$, and $FB_{47}$.

FIG. 2 shows a recombinant DNA of the invention encoding a typical reduced-binding analog of a Protein A binding domain ($FB_{29}$) useful in the invention and its amino acid sequence, including a methionine residue (start) at the N-terminus and a Pro, Pro, Cys, Ala, Ala spacer sequence used to couple the binding site to an immobilized matrix; and FIG. 3 are graphs showing the relative binding affinities of native FB and two repesentative FB analogs for complex and sol-Ab.

DESCRIPTION

The intermolecular forces involved in the interaction of the binding regions of Protein A and the Fc portion of IgG were studied from x-ray crystallographic data and computer generated binding energies. A complex consisting of a Protein A binding fragment (FB) and the Fc fragment of human IgG was crystallized, and the three dimensional structure was determined (Deisenhofer et al., 1978, Hoppe-Seyler's Z. Physiol Chem. 359:975–985; Deisenhofer, 1981, Biochemistry, 20:2361–2378). In addition, computer generated estimates of binding energies for the interaction of FB and Fc were made.

These data and information permitted the construction of a working model or rough atlas of contact points showing for each residue in FB and Fc, the atoms in the complementary molecules which are within a distance of 4 angstroms. Examination of the positions of polar and charged residues at the contact interface by computer graphics revealed that a number of positive and negative charges become buried at the interface of the two molecules (i.e., in a medium of small dielectric constant), and it was hypothesized that their electrostatic interaction might contribute significantly to the binding energy. Further analysis indicated no obvious pairs of opposing charges on the complementary surfaces of the molecules, suggesting that the binding mechanism did not involve simple neutralization of opposing charges.

The amino acid sequence of the FB region of native Protein A is shown in FIG. lA. The molecule contains two alpha helical regions which are underlined. Crystallographic studies have revealed that these helices are intimately associated with the Fc region of IgG during binding. The starred amino acids indicated in FIG. lA are those which have been determined to be involved in the binding most directly, i.e., to lie within about 4 angstroms from a residue of Fc in the Fc-FB complex.

From the foregoing information, it was predicted what changes in the amino acid sequence of the FB domain of the Protein A molecule likely would reduce its affinity for IgG, and analogs of the FB region were designed to test the predictions. The amino acid sequences of several of the analogs are presented in FIG. lB. These analogs were shown to have affinities for soluble IgG with $K_a$'s of between $1\times10^3M^{-1}$ and $5\times10^6M^{-1}$.

The approach used in designing such analogs can be understood better by a review of FIG. 1B. The protein labeled $FB_{58}$ is the native, or wild type, FB sequence. $FB_{TF}$ may be produced by cleaving the native form of the protein fragment with trypsin, which cleaves at the $Lys^7$-$Glu^8$ bond. $FB_{58}$ has a $K_a$ for Fc of about $5\times10^7M^{-1}$; $FB_{TF}$ has a $K_a$ for FC of about $5\times10^6$ $M^{-1}$. The remaining analogs are made by expression of an appropriate DNA. All comprise truncated analogs of the native fragment. The approximate affinities of these analogs for Fc in liters per mole are, respectively $FB_{36}$, $K_a=2\times10^3$; $FB_{29}$, $4\times10^2<K_a<2\times10^3$; $FB_{40}$, $6\times10^3<K_a<2\times10^4$; $FB_{47}$, $K_a=2\times10^3$. Oligomers of the various analogs comprise moieties having high affinity for complex, e.g., greater than $10^7M^{-1}$ and preferably greater than $10^8M^{-1}$, and low affinity for Fc, e.g., less than about $10^7M^{-1}$, and preferably less than $10^5M^{-1}$. Multiple point attachment requires a spacing between binding domains on the oligomer of at least 52 angstroms (center to center). Multiple point interaction with comp lex will also occur if such analogs are immobilized on a surface at a sufficient density such that two or more Fc's in a complex can react simultaneously.

As will be appreciated by those skilled in the art, the Fc affinity of the FB fragment does not depend on precise duplication of the amino acid sequence and encoding DNA sequence set forth in FIG. 1. Other DNAs which encode the same amino acid sequence may be used. Fragments of the FB of FIG. 1 comprising less than the full amino acid sequence retain some binding activity. It is also contemplated that amino acids in the sequence may be replaced while retaining significant binding activity. Other modified amino acid sequences, including analogs of the A, C, D, or E binding domains of Protein A, and related sequences from functionally similar bacterial proteins such as fragments of protein G from Streptococcus species are within the scope of the present invention. Such species having a binding affinity of at least $5\times10^2M^{-1}$ have utility.

There is but a single binding site recognized by Protein A on each of the heavy chains of IgG constituting the Fc region. Complex, on the other hand, presents an array of binding sites in close proximity. This structural difference is exploited to increase selectivity of the complex binding moiety by designing repeats or oligomers of analogs of the binding sites of Protein A or other structures comprising adjacent binding domains, each of which individually have a relatively low affinity for Fc. Such an oligomer has a low affinity for species having a single binding site, such as free IgG, but a higher affinity for species having multiple binding sites, such as complex. The affinity constant of such oligomers is the product of the individual affinities $K_o$, of the repeating units if binding can occur independently at each site, where $K_o$ is the intrinsic binding constant defined using molal concentrations of reactants. Thus, an analog having an affinity for Fc of, for example, $1 \times 10^3 M^{-1}$, can be used to produce, for example, a trimer, having an affinity for the Fc of a free immunoglobulin molecule of the same $1 \times 10^3 M^{-1}$, but an affinity for complex of approximately $1 \times 10^9 M^{-1}$. If the formation of one analog-Fc binding pair interferes with the formation of others, then the observed $K_a$ will be less than $(K_o)^3$ but still higher than $K_o$.

Figure 3:
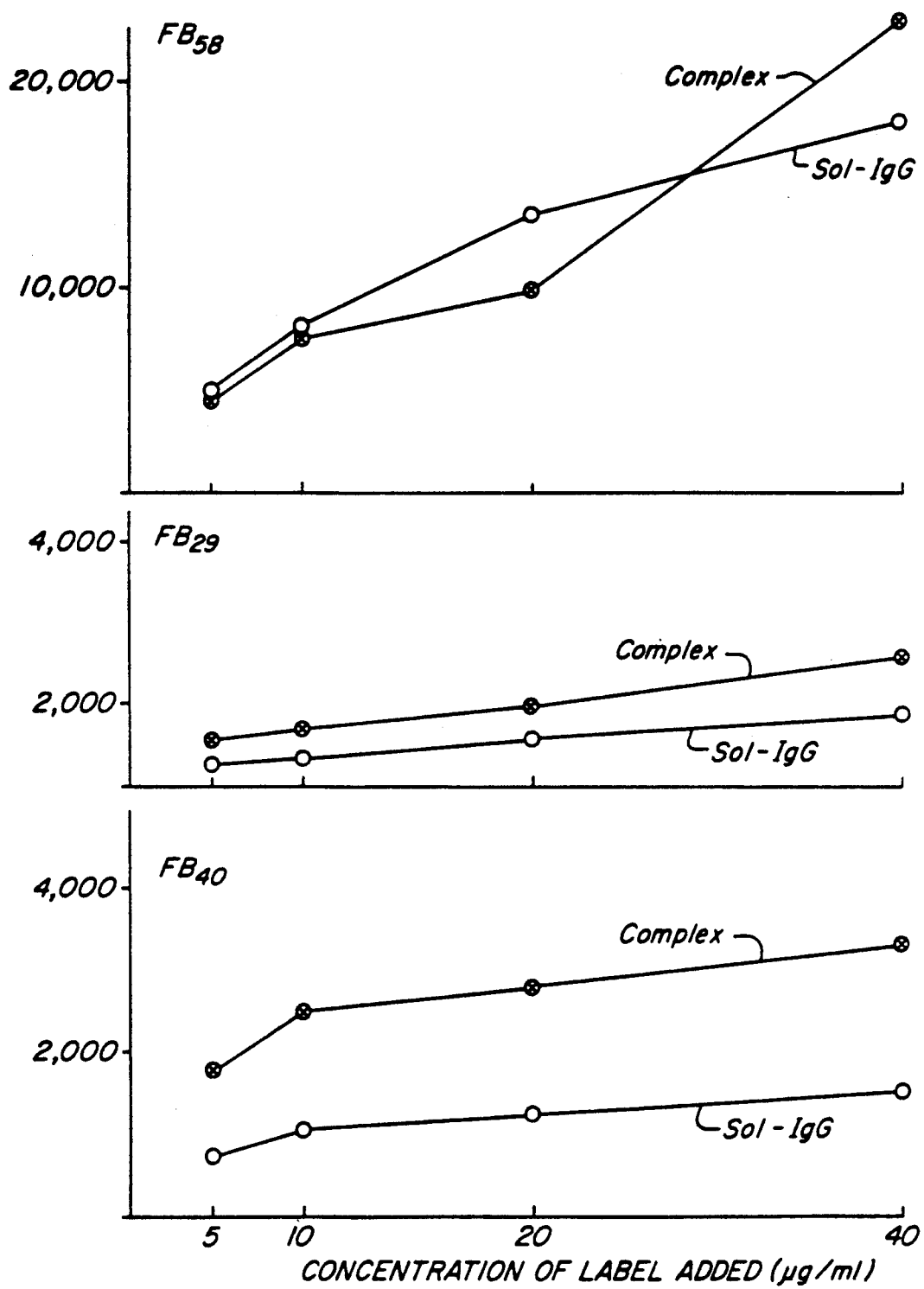

It should be noted that Protein A itself may be regarded as a linear array of binding sites. However, presumably because of steric hindrance, only two sites on a single Protein A molecule can bind at the same time under the best of conditions, and Protein A does not bind selectively to complex to any significant extent.

Genes encoding these Protein A binding site analogs may be designed based on the amino acid sequences of the analogs shown in FIG. 1B, or on other known sequences of Protein A, Protein G, or other binding domains, and prepared using known recombinant DNA techniques by assembly of synthetic oligonucleotides or other methods known per se. The DNA and amino acid sequence of a typical FB analog is presented in FIG. 2. It corresponds to the structure $FB_{29}$ set forth in FIG. 1B, and comprises a start site (MET), a Pro, Pro, Cys, Ala, Ala sequence used, through the Cys residue, to bind to an immobilization matrix, and then 29 residues of native FB, spanning the two helical regions, and including seven of the nine residues thought to be most important to binding.

Generally, analogs such as those shown in FIG. 1B may be expressed as fusion proteins containing a leader peptide for increased expression in *E. coli*, followed, as exemplified by FIG. 2, by a methionine residue which serves as a cyanogen bromide cleavage site for release of the leader peptide, and a cysteine residue located at or close to the analog's amino terminus to facilitate directed immobilization of the reduced-binding analog to a solid support. Of course, many other production techniques would be apparent to the skilled molecular biologist. Such constructs are designed for use in the production of an immunosorbent material comprising a matrix of inert, relatively high surface area particles such as Sepharose beads (cross-linked dextran) or other biologically compatible material.

Provided the analog is bound to the matrix at least at a minimal threshold concentration, the surface density of the binding sites permit multiple attachments to immune complexes Stated differently, unless the analogs are disposed on a matrix at such a low density that their spacing exceeds the distance between binding sites on comPlex, this type of material will bind complex preferentially to free immunoglobulin. This is in contrast to the native intact Protein A molecule, which at best permits macromolecular aggregate formation having the empirical formula [(IgG)$_4$ (Protein A)$_2$]. The concentration of analog which works best should be determined empirically, and will depend on such factors as the surface area of the matrix material, mode of coupling, the specific nature of the analog used, and the size of the immune complex.

Alternatively, the reduced binding analogs may be expressed as a Protein A-like molecule (oligomer) comprising multiple reduced binding domains spaced far enough apart by incorporated amino acid spacer sequences to permit the formation of multiple binding pairs. In this regard, the minimal distance between the centers of two active binding sites should be about 52 angstroms. These may then be immobilized to produce an immunosorbent material with the desired selectivity.

Functionally, an "immune complex" can be described as a molecular aggregate containing multiple Fc's of IgG; the aggregate or complexes may be the result of antigen-antibody bridging, heat aggregation, or chemical cross-linking. Because of the potential instability of antigen-antibody aggregates and heat aggregates, covalently cross-linked aggregates of human IgG were used as a model for natural complex in the reduction to practice of the present invention. Human IgG is cross-linked with carbodiimide, and aggregates of different sizes are recovered by gel filtration chromatography. The aggregates used in the experiments reported here have a molecular weight of approximately 600,000 daltons, equivalent to a tetramer of IgG. Prior to use, the aggregates were diluted in human serum having a low endogenous level of circulating immune complexes.

The invention will be understood further from the following non-limiting examples, which are intended to be illustrative and not restrictive.

Preparation of Transformants

The molecular biologY and microbiology involved in the construction of the gene encoding the $FB_{29}$ analog of Protein A is provided as an example of the molecular biology and microbiology involved in a gene construction.

The gene coding for the $FB_{29}$ analog was constructed by truncation and/or substitution of the $FB_{58}$ parent gene at both the N-terminus and C-terminus. The $FB_{58}$ gene had previously been synthesized by ligation of oligonucleotides. A plasmid preparation containing the DNA sequence coding for the $FB_{58}$ (FIG. 1) was digested with EcoRI and MluI restriction enzymes in preparation for the alteration of the gene at its N-terminus. The double cut plasmid preparation was separated from single cut and uncut molecules by polyacrylamide gel electrophoresis. Following electroelution, ethanol precipitation and resuspension, the EcoRI/MluI digested plasmid was ligated with oligonucleotides synthesized with the desired DNA sequence designed to code for the desired Protein sequence. Each end of the sequence was designed to be complementary to the EcoRI and MluI sites generated within the plasmid by these restriction enzymes. The ligation mixture was transformed into competent *E. coli* cells by standard microbiological procedures. Resulting colonies were screened for the presence of the altered N-terminus by restriction analysis. Verification of the desired sequence was accomplished by DNA sequencing (Sanger dideoxy method).

Similarly, the C-terminus of this altered gene was truncated by digesting the plasmid with HindIII and PstI. Oligonucleotides of the desired sequence (designed with compatible ends for ligation into the HindIII and PstI sites) were ligated into the double-cut plasmid. Following ligation, transformation, screening, and sequencing, the final gene sequence (FIG. 2) was prepared for expression by inserting a promoter and appropriate leader peptide to the N-terminus of the gene.

Preparation of Inoculum for Bacterial Fermentation

A frozen stock of *E. coli* containing the desired plasmid is inoculated into 59 ml of Luria broth containing 10 g/l tryptone, 10 g/l yeast extract, 5 g/l NaCl, and 1 ml/l tetracycline stock (10 mg/ml in 95% ethanol) in a 1 liter baffled shaker flask. The culture is incubated on a rotating platform at 200 rpm for 17 hr at 37° C. The fermenter is inoculated with the entire 200 ml.

Fermentation of *E. coli*

The above stationary phase culture is inoculated into 10 liters of medium consisting of 11 g/l $Na_2HPO_4$, 15 g/l D-glucose, 5 g/l acid hydrolysate, 3 g/l $KH_2PO_4$, 1 g/l $NH_4Cl$, 0.5 g/l NaCl, 5 ml/l trace mineral mix (13.3 ml concentrated HCl, 5.4 g/l $FeCl_3.6H_2O$, 1.44 g/l $ZnSO_4.7H_2O$, 1.0 g/l $MnCl_2.4H_2O$, 0.25 g/l $CuSO_4.5H_2O$, and 0.062 g/l $H_3BO_3$), 0.5 ml/l 1M $MgSO_4.7H_2O$, 1.4 ml/l 1M $CaCl_2.2H_2O$, 0.2 ml/l 1M $Na_2MoO_4.2H_2O$, 0.5 ml/l tryptophan (10 mg/ml in 100 mM acetic acid), 1.0 ml/l tetracycline (10 mg/ml), 2.5 ml/l niacin (10 mg/ml), 2.5 ml/l biotin (0.5 mg/ml in 95% ethanol) and 0.2 ml/l antifoam, pH 7.0 in a 14 liter fermenter. The bacterial culture is agitated at 700 rpm and incubated at 35° C. The pH of the culture medium is maintained in the range of 6.85 to 7.15 by the addition of $NH_4OH$. The culture is sparged with filtered air at a flow rate of 10 liters per minute.

The culture is induced for expression of the protein by addition of 3B-indoleacrylic acid (IAA) to a final concentration of 20 mg/ml culture when the absorbance at 600 nm is approximately 4. The culture is induced a second time at 20-22 hours post-inoculation to a final concentration of 20 mg/ml IAA. At ten hours post-inoculation, the cells are fed with a solution of 500 g/l D-glucose, 2 g/l casamino acids, 50 ml/l trace mineral mix (see above), 5 ml/l 1M $MgSO_4.7H_2O$, 14 ml/l 1M $CaCl_2.2H_2O$, 2 ml/l 1M $NaMoO_4.2H_2O$, 20 ml/l biotin stock solution (see above) and 20 ml/l niacin stock solution (see above), at a flow rate of 125 ml/hr. The feed is on for 0.5 hours and off for 2.5 hours consecutively until the fermentation is terminated at 30 hours post-inoculation.

At the end of the fermentation, the culture is decanted into a 20 liter carboy and concentrated to 1 liter with an Amicon hollow fiber ultrafiltration unit. After diafiltration with 5.0 l of deionized water, the cells are pelleted by centrifugation at 11,300×g for 10 min. After decanting the supernatant, the cell pellet is transferred to appropriate containers and stored at −70° C.

Preparation of Inclusion Bodies

One hundred grams of frozen cell paste is resuspended in 1 liter of deionized water. The cells are lysed in a homogenizer operating at 5000 psi. The partially lysed cells are stored of ice for 15 minutes and are passed through the homogenizer a second time under identical conditions. Inclusion bodies and cell debris are pelleted by centrifugation at 3500×g for 30 min at 4° C.

Purification of Analogs

The fusion protein is solubilized from the inclusion bodies in buffer consisting of 40 mM Tris-HCl, 1 mM EDTA and 8M urea, pH 8.0. A volume of 25 ml of buffer for each gram of inclusion bodies is added; solubilization is facilitated by stirring and homogenization. Once the fusion protein is in solution, the urea is removed by dialysis against 1 mM EDTA pH 8.0 in $dH_2O$ overnight at 4° C. The dialyzed material is adjusted to 0.1M HCl by the addition of concentrated acid, and cyanogen bromide (0.25 g/g cell paste) is added to cleave the Protein A analog from the leader peptide. The reaction is incubated, with stirring, for 4–6 hr in the dark at room temperature. Unreacted cyanogen bromide and volatile by-products are removed by lyophilization. The residue is resuspended in deionized water, and the pH of the solution is adjusted to 8.0 by the addition of 1 N NaOH. After stirring at room temperature for 2 hr while maintaining the pH, the digest is dialyzed overnight against 20 mM Tris-HCl, 1mM EDTA, pH 8.0. The digest is reduced by the addition of 1 mM dithiothreitol (DTT) prior to ion exchange chromatography.

The digest is then chromatographed on an anion exchange column consisting of Whatman DE-52 cellulose equilibrated in 20 mM Tris-NaCl, 1 mM EDTA, and 1 mM DTT, pH 8.0 (column buffer). The sample is loaded in column buffer. Protein eluting from the column is monitored at 280 nm and collected in 20 ml fractions. Bound proteins are eluted using a gradient of 0–500 mM NaCl in column buffer. Individual fractions are evaluated for the presence of the desired analog by analytical C-18 reverse phase high performance liquid chromatography (HPLC), sodium dodecyl sulfate-polyacrylamide gel elecrophoresis (SDS-PAGE) and/or radioimmunoassay (RIA) using chicken anti-Protein A antibody (described below). The appropriate fractions are pooled, concentrated, and dialyzed against 1 mM EDTA in distilled water. The sample is again reduced with 1 mM DTT and loaded onto a preparative C18 column equilibrated in 25% acetonitrile in $dH_2O$ adjusted to pH 2.0 with trifluoroacetic acid. Bound material is eluted from the column using a 25–45% gradient of acetonitrile. Identification of the analog is confirmed by co-elution from an analytical C18 column with an aliquot of a previously analyzed lot of recombinant analog and/or amino acid analysis and sequencing. The purity of the analog is assessed by analytical reverse phase chromatography Fractions having the desired purity are pooled and lyophilized.

RIA for Protein A analogs

A "sandwich" radioimmunoassay (RIA) employing chicken anti-FB has been used to identify and quantitate reduced binding analogs in samples generated during purification. Briefly, chicken anti-FB, diluted to a concentration of 2.5 μg/ml in borate buffered saline, pH 8.0 (BSB), is adhered to the wells of polyvinyl chloride microtiter plates by incubation at 37° C. for 1 hr in a humid atmosphere. The unbound protein is removed, and the remaining protein binding sites are blocked by incubation of the plates with 1% nonfat skim milk in BSB for 1 hr at 37° C. Varying dilutions of Protein A analogs of known concentration or unknown samples are added to the wells for 4–18 hr at room temperature. Upon completion of the binding period, unbound proteins are removed by washing individual wells with BSB. $^{125}$I-labeled chicken anti-FB, having a concentration of 2.5 μg/ml and a specific activity of 2500 cpm/ng, is added to each well to detect bound analogs. The plates are incubated overnight at room temperature, washed, and the radioactivity determined. A standard curve is drawn by plotting cpm bound per well versus concentration of analog. The concentration of analog within an unknown sample is determined from the linear portion of the curve. The sensitivity of this assay is 5-100 ng/ml for the native FB molecule and 5-100 μg/ml for the reduced binding analogs.

Competitive RIA to Assess Analog Binding to IgG

Human IgG, diluted to a concentration of 20 μg/ml in BSB, is adhered to the wells of polyvinyl chloride microtiter plates. The remaining protein binding sites are blocked by the addition of 1% skim milk in BSB. Excess protein solution is discarded, and dilutions of FB or its analogs, having known protein concentrations, are added to the wells. After incubation for 30 min, a constant quantity of $^{125}$I-labeled FB diluted to 0.05 μg/ml is added to each well. The plates are incubated overnight at room temperature in a humidified atmosphere. Plates are washed to remove unbound radioactivity, air dried, and the individual wells are cut and counted in a gamma scintillation spectrometer. Values for % Inhibition are calculated at each analog concentration using the following formula:

$$\% \text{ Inhibition} = \frac{cpm_{100} - cpm_{test} \times 100}{cpm_{100}}$$

where $cpm_{100}$ represents the counts bound in wells without inhibitor and $cpm_{test}$ represents the counts bound in wells containing known amounts of FB or its analogs. Binding curves are constructed for FB and its analogs by plotting % inhibition versus inhibitor concentration; th quantities of each analog required for 50% inhibition of binding are determined graphically. Binding constants of the reduced binding analogs are calculated as follows:

$$K(FB_x) = \frac{K(FB)}{[FB_x]/[FB]}$$

where $K(FB_x)$ is the binding constant for the analog $FB_x$, K(FB) is the binding constant for the native fragment B molecule (assumed to be $5 \times 10^7 M^{-1}$ Langone, 1982), and $[FB_x]$ and [FB] are the molar concentrations of $FB_x$ and FB required for 50% inhibition of binding.

Selective Binding of Immune Complexes using Monomeric

Protein A Analogs $FB_{58}$ (native FB) or a reduced binding analog is diluted in 0.1M carbonate buffer, pH 9.0, and adhered to the wells of polystyrene microtiter plates for 2 hr at 37° C. Varying the analog concentration between 1.5 and 100 μg/ml has little or no effect on the subsequent binding of $^{125}I$-labeled soluble IgG or heat aggregated IgG. The remaining protein binding sites are blocked by incubation with 1% skim milk for 1 hr. After removal of the blocking solution, soluble IgG diluted in 1% skim milk is added for 2 hr at room temperature to saturate immunoglobulin binding sites. The excess is removed by washing the wells with BSB; varying concentrations of $^{125}I$-labeled soluble IgG or aggregated IgG (adjusted to the same specific activity) are added to the wells and incubation is continued overnight. Comparison, for the two labels, of absolute counts bound in wells coated with $FB_{58}$ or an analog is used to assess selective binding. A representative experiment comparing the ability of $FB_{58}$, $FB_{29}$ and $FB_{40}$ (See FIG. 1) to bind $^{125}I$-IgG and $^{125}I$-aggregated IgG is shown in FIG. 3. In wells coated with $FB_{58}$, similar and significant quantities of both ligands are bound at ligand concentrations between 5 and 40 μg/ml and a saturation concentration of soluble IgG of 1 mg/ml. Attempts to abrogate the binding of $^{125}I$-IgG to $FB_{58}$ by increasing the saturation concentration of soluble IgG to 5 mg/ml were unsuccessful (due to working around the equilibrium concentration of soluble IgG), although the absolute number of counts bound was decreased. In wells containing $FB_{29}$ and $FB_{40}$, the absolute number of counts of both ligands is decreased compared to $FB_{58}$-containing wells, but significantly greater quantities of $^{125}I$-aggregated IgG is bound compared to $^{125}I$-soluble IgG. In this configuration, more counts are bound in wells containing $FB_{40}$ than $FB_{29}$. Increasing the saturation concentration of soluble IgG from 1 to 5 mg/ml enhanced selective binding in wells coated with the analogs.

SELECTIVE REMOVAL OF IMMUNE COMPLEXES USING

IMMOBILIZED MONOMERIC PROTEIN A ANALOGS

Immobilization

Sepharose CL-4B (Pharmacia) is activated as follows. The gel is washed sequentially with water, dioxane/water mixtures, and anhydrous dioxane prior to the addition of anhydrous recrystallized 4-dimethylam:inopyridine (DMAP). A solution of tosyl chloride in anhydrous dioxane is then added and the mixture is shaken at room temperature for 15 min. The mixure is filtered with anhydrous .dioxane to remove any unreacted DMAP and tosyl chloride. A 0.5 M solution of diaminodipropylamine (DADPA) in anhyrdrous dioxane is then added and the mixture is shaken overnight under nitrogen at 4° C. The gel is filtered and sequentially washed with anhydrous dioxane, dioxane/1 mM HCl mixtures, and finally water. After additional washing with 0.1M sodium phosphate buffer, pH 6.7, containing 10 mM EDTA, a freshly made solution of the heterobifunctional cross-linker, m-maleimidobenzoyl sulfosuccinimide (sulfo-MBS) is added and the gel is mixed for 2 hr at room temperature. The gel is washed again with 0.1M sodium phosphate, 10 mM EDTA, pH 6.7 and then with 0.1M sodium acetate, 10 mM EDTA, pH 5.0. The activated gel with the attached sulfo-MBS is separated into aliquots, and mixed with solutions containing various concentrations of a Protein A analog. The mixtures are agitated at room temperature for 90 min, and washed with sodium acetate-EDTA buffer, pH 5.0. Unreacted sulfo-MBS is blocked for 90 min by the addition of 0.1M 2-mercaptoethanol in the same buffer. After blocking, the gel is washed with sodium acetate-EDTA buffer, pH 5.0, and then with 10mM sodium phosphate, 150 mM NaCl, 2 mM EDTA, pH 7.3. The gel is stored at 4° C. in the sodium phosphate buffer with 0.02% sodium azide until use.

Immune Complex Assay

Complex is quantitated using the enzyme-linked immunoassay kit marketed by Cytotech according to the manufacturer's instructions. Three standards of heat-aggregated IgG, are included in the kit to allow the construction of a standard curve. The values of unknown samples are determined from the standard curve; sera containing less than 4 μg equivalents (Eq)/ml are considered normal, while those with higher levels are considered elevated.

Soluble Human IgG RIA

Soluble IgG levels are quantitated by RIA. Briefly, specifically purified goat anti-human-IgG, diluted to a concentration of 5 µg/ml, is absorbed to the wells of PolYvinyl chloride microtiter plates. After blocking non-specific protein binding sites with 1% lowfat dry milk, aliquots of IgG standards or dilutions of unknown samples are added to the well and the plates are incubated at room temperature for 4 hr. Following extensive washing to remove unbound material, a constant amount of $^{125}$I-labeled goat anti-IgG is added to each well. At the end of an 18-24 hour incubation at room temperature, the plates are washed, dried, cut and counted. A standard curve is constructed using samples of known soluble IgG concentrations between 7.5 and 640 ng/ml. Unknown samples are assayed in triplicate wells at four different dilutions. The concentration of IgG in an unknown is calculated from the standard curve; those dilutions falling on the linear portion of the curve are corrected for dilution and averaged to obtain the reported IgG concentration. This assay detects IgG in complex, in addition to sol-Ab, although complex is detected less efficiently on a µg/ml basis.

Selective Removal of Circulating Immune Complex Using

Sepharose-Coupled Protein A Analogs

Aliquots of each Sepharose-FB analog preparation are placed in Eppendorf centrifuge tubes. The gel is washed twice and the supernatants discarded. One hundred µl samples of chemically aggregated IgG diluted in normal human serum (CAG/NHS) or normal human serum similarly diluted with buffer (NHS) are added to the gel, mixed and incubated for varying amounts of time at 37° C. Similar results are obtained when the time of adsorption is varied between 5 and 120 min and the temperature is maintained at 37° or 25° C. The supernatants are removed to separate tubes, and the gel samples are washed by the addition of 100 µl of buffer. The wash is pooled with the initial supernatant. Control samples are absorbed on Sepharose to which no Protein A analog has been coupled. Subsequently, each sample is diluted appropriately and complex and sol-Ab levels are determined using the Cytotech EIA kit and IgG RIA, respectively.

Table I set forth below presents the results of an experiment in which the effect of concentration of immobilized analog on selective removal of immune complexes was determined.

TABLE I

| Sepharose | Sample | CIC Level, µg/ml | HuIgG Level, mg/ml |
|---|---|---|---|
| None | CAG/NHS | 21.0 | 4.03 |
| Control | CAG/NHS | 18.3 [13][1] | 3.70 [8] |
| FB$_{58}$, 4 mg/ml | CAG/NHS | 8.0 (56)[2] | 0.90 (76) |
| FB$_{58}$, 3 mg/ml | CAG/NHS | 7.0 (62) | 0.99 (73) |
| FB$_{58}$, 2 mg/ml | CAG/NHS | 9.1 (50) | 1.49 (60) |
| FB$_{58}$, 1 mg/ml | CAG/NHS | 10.2 (43) | 2.11 (43) |
| FB$_{29}$, 4 mg/ml | CAG/NHS | 7.0 (62) | 3.55 (4) |
| FB$_{29}$, 3 mg/ml | CAG/NHS | 8.0 (56) | 3.72 (−1) |
| FB$_{29}$, 2 mg/ml | CAG/NHS | 10.3 (44) | 3.04 (18) |
| FB$_{29}$, 1 mg/ml | CAG/NHS | 12.7 (31) | 3.73 (−8) |
| None | NHS | 2.2 | 3.82 |
| Control | NHS | 1.6 | 3.10 [19] |
| FB$_{58}$, 4 mg/ml | NHS | 0.2 | 0.92 (70) |
| FB$_{58}$, 3 mg/ml | NHS | ND[3] | 1.04 (66) |
| FB$_{58}$, 2 mg/ml | NHS | ND | 1.07 (65) |
| FB$_{58}$, 1 mg/ml | NHS | ND | 1.97 (36) |
| FB$_{29}$, 4 mg/ml | NHS | 0.8 3.39 | (−9) |
| FB$_{29}$, 3 mg/ml | NHS | ND | 3.26 (−5) |
| FB$_{29}$, 2 mg/ml | NHS | ND | 3.46 (−13) |
| FB$_{29}$, 1 mg/ml | NHS | ND | 2.78 (10) |

[1]Number in brackets represents the % reduction compared to an unadsorbed sample similarly handled.
[2]Number in parentheses represents the % reduction compared to the sample absorbed on control Sepharose.
[3]Not determined.

Absorption of CAG/NHS with each preparation of Sepharose-FB$_{58}$ or FB$_{29}$ decreased complex concentration measurable in the cotnrol sample from 18.3 µg Eq/ml to between 7 and about 13 µg Eq/ml. Analog concentrations of 3 and 4 mg/ml of gel are capable of removing larger quantities of complex compared to lower analog concentrations. After adsorption of NHS on gel derivitized with FB$_{58}$, human sol-Ab levels are decreased to 36-70% of control values. In contrast, adsorption of samples of NHS on FB$_{29}$ derivitized gel resulted in little or no decrease in levels of sol-Ab (−13% to 10% reduction).

A subsequent experiment was performed to determine whether complex levels could be decreased in a dose dependent manner by adsorption with inceasing quantities of immobilized Protein A analogs. Volumes of conjugated Sepharose, between 25 and 200 µl of packed gel, were distributed into tubes. The analog to gel concentration of both FB$_{58}$ and FB$_{29}$ in this experiment was 4 mg/ml gel. One hundred microliter samples of CAG/NHS were added to each tube, mixed and incubated at room temperature for 10 min. The supernatants were removed, and the gel samples washed and processed as described above. The results of this experiment are presented in Table II which is set forth below, wherein CIC indicates circulating immune complex and HuIgG indicates human immunoglobulin.

TABLE II

| Volume Sepharose | Control Sepharose | | FB$_{58}$-Sepharose[1] | | FB$_{29}$-Sepharose[1] | |
|---|---|---|---|---|---|---|
| | CIC | HuIgG | CIC | HuIgG | CIC | HuIgG |
| 25 µl | 29.68[2] | 4.25[3] | 21.52 (27)[4] | 2.65 (38) | 20.40 (31) | 4.68 (−10) |
| 50 µl | 30.92 | 4.43 | 19.60 (37) | 1.75 (60) | 12.40 (60) | 3.73 (16) |
| 100 µl | 28.68 | 3.57 | 13.20 (54) | 0.77 (78) | 10.12 (65) | 4.19 (−17) |
| 150 µl | 23.68 | 3.64 | 5.60 (76) | 0.46 (87) | 5.92 (75) | 3.56 (2) |
| 200 µl | 26.40 | 2.99 | 2.72 (90) | 0.34 (89) | 4.92 (81) | 3.01 (−1) |

[1]The concentration of analog to gel used in these experiments was 4 mg/ml.
[2]CIC levels are reported in µg Eq/ml.
[3]HuIgG levels are reported in mg/ml.
[4]The values in parentheses are the percent reduction in levels compared to the same volume of control Sepharose.

Absorpiton of CAG/NHS on increasing quantities of FB$_{58}$- or FB$_{29}$-Sepharose resulted in a dose dependent reduction in CIC levels, form 27 to 90% of control values. Sol-Ab levels were similarly decreased after adsorption on Sepharose-FB$_{58}$; between 38 and 89%. In contrast, the soluble IgG levels of samples absorbed on Sepharose-FB$_{29}$ showed little or no reduction (between −17 and 16% of control values).

The invention may be embodied in other specific forms, and other embodiments are within the following claims.

What is claimed is:

1. A DNA molecule which encodes a polypeptide comprising plural, spaced apart binding domains of protein A or protein G, individual said domains binding with a site on human Fc with a binding constant less than $10^7 M^{-1}$, and the spacing of said domains being such that a plurality of said domains together bind to a corresponding plurality of sites on plural human immunoglobulins aggregated in a complex by multiple point attachment with a net binding constant greater than $1 \times 10^7 M^{-1}$.

2. A DNA molecule of claim 1 wherein at least one of said domains comprises a polypeptide homologous to an Fc bnding portion of Staphylococcal Protein A.

3. A DNA molecule of claim 1 encoding a cysteine residue adjacent the amino terminus of said polypeptide.

* * * * *